US009012150B2

(12) United States Patent
Smilansky

(10) Patent No.: US 9,012,150 B2
(45) Date of Patent: Apr. 21, 2015

(54) METHODS FOR EVALUATING RIBONUCLEOTIDE SEQUENCES

(75) Inventor: Ze'ev Smilansky, D.N. Emek Sorek (IL)

(73) Assignee: Anima Cell Metrology, Bernardsville, NJ (US)

(*) Notice: Subject to any disclaimer, the term of this patent is extended or adjusted under 35 U.S.C. 154(b) by 1349 days.

(21) Appl. No.: 11/569,476

(22) PCT Filed: May 26, 2005

(86) PCT No.: PCT/IL2005/000540
§ 371 (c)(1),
(2), (4) Date: Sep. 11, 2007

(87) PCT Pub. No.: WO2005/116252
PCT Pub. Date: Dec. 8, 2005

(65) Prior Publication Data
US 2009/0081643 A1 Mar. 26, 2009

Related U.S. Application Data

(60) Provisional application No. 60/574,210, filed on May 26, 2004.

(51) Int. Cl.
C12Q 1/68 (2006.01)
G06F 19/10 (2011.01)
B82Y 5/00 (2011.01)
B82Y 10/00 (2011.01)

(52) U.S. Cl.
CPC ...... C12Q 1/68 (2013.01); B82Y 5/00 (2013.01); B82Y 10/00 (2013.01); C12Q 1/6818 (2013.01); C12Q 1/6834 (2013.01); C12Q 1/6869 (2013.01)

(58) Field of Classification Search
None
See application file for complete search history.

(56) References Cited

U.S. PATENT DOCUMENTS

| | | | |
|---|---|---|---|
| 5,082,767 A | 1/1992 | Hatfield | |
| 5,626,058 A | 5/1997 | Karpowich | |
| 5,643,722 A | 7/1997 | Rothschild | |
| 5,706,498 A | 1/1998 | Fujimiya | |
| 5,777,079 A | 7/1998 | Tsien | |
| 5,856,928 A | 1/1999 | Yan | |
| 5,922,858 A | 7/1999 | Rothschild | |
| 6,189,013 B1 | 2/2001 | Maslyn | |
| 6,210,941 B1 | 4/2001 | Rothschild | |
| 7,015,486 B1 | 3/2006 | Sarbach | |
| 7,288,372 B2 | 10/2007 | Olejnik | |
| 7,388,125 B2 | 6/2008 | Ristic | |
| 7,807,349 B2 | 10/2010 | Smilansky | |
| 2003/0092031 A1 | 5/2003 | Rothschild | |
| 2003/0219780 A1 | 11/2003 | Olejnik | |
| 2003/0219783 A1 | 11/2003 | Puglisi | |
| 2004/0023256 A1 | 2/2004 | Puglisi | |
| 2004/0023874 A1 | 2/2004 | Burgess | |
| 2004/0235175 A1 | 11/2004 | Gaudernack | |
| 2005/0118151 A1 | 6/2005 | Larsen | |
| 2005/0157294 A1 | 7/2005 | Hopkins | |
| 2005/0164264 A1 | 7/2005 | Shipwash | |
| 2005/0267037 A1 | 12/2005 | Anderson | |
| 2006/0292566 A1 | 12/2006 | Frazer | |
| 2007/0021597 A1 | 1/2007 | Edwards | |
| 2007/0134814 A1 | 6/2007 | Kajander | |
| 2009/0081643 A1 | 3/2009 | Preminger | |
| 2010/0317121 A1 | 12/2010 | Smilansky | |
| 2011/0262899 A1 | 10/2011 | Cooperman | |
| 2012/0183957 A1 | 7/2012 | Smilansky | |

FOREIGN PATENT DOCUMENTS

| | | |
|---|---|---|
| DE | 4410655 | 9/1995 |
| EP | 1428016 | 4/2008 |
| FR | 2798143 | 3/2001 |
| WO | 94/02595 | 2/1994 |
| WO | 01/16375 | 3/2001 |
| WO | 03/025554 | 3/2003 |
| WO | 03/052067 | 6/2003 |
| WO | 03/057164 | 7/2003 |
| WO | 03/064604 | 8/2003 |
| WO | 2004/050825 A2 | 6/2004 |
| WO | 2005/001062 | 1/2005 |
| WO | 2005/116252 | 12/2005 |
| WO | 2007/002758 | 1/2007 |
| WO | 2008/028298 | 3/2008 |
| WO | 2009/047760 | 4/2009 |

OTHER PUBLICATIONS

Petitjean et al. The duplicated *Saccharomyces* gene SSM1 encodes a eucaryotic homolog of the eubacterial and achaebacterial L1 ribosomal proteins. Molecular and Cellular Biology, vol. 15, No. 9, pp. 5071-5081, Sep. 1995.*
Bakin AV. Et al. "Spatial organization of template polynucleotides on the ribosome determined by fluorescence methods". J Mol Biol. Sep. 20, 1991;221(2):441-453.
Erdogan F. et al. "Detection of mitochondrial single nucleotide polymorphisms using a primer elongation reaction on oligonucleotide microarrays". Nucleic Acids Res. Apr. 1, 2001;29(7):E36.
Garber K. "Genomic medicine. Gene expression tests foretell breast cancer's future". Science. Mar. 19, 2004;303 (5665):1754-1755.
Ha, T, Single-molecule fluorescence resonance energy transfer, Methods 25, 78-86 (2001).
Mascarenhas J. et al. "Specific polar localization of ribosomes in *Bacillus subtilis* depends on active transcription". EMBO Rep. Aug. 2001;2(8):685-689.
Odom AW. Et al. "Movement of tRNA but not the nascent peptide during peptide bond formation on ribosomes". Biochemistry. Dec. 4, 1990;29(48):10734-10744.
Pelletier J. et al. "The involvement of mRNA secondary structure in protein synthesis". Biochem. Cell Biol. Jun. 1987;65 (6):576-581.
Robbins D. et al. "Comparison of ribosomal entry and acceptor transfer ribonucleic acid binding sites on *Escherichia coli* 70S ribosomes. Fluorescence energy transfer measurements from Phe-tRNAPhe to the 3' end of 16S ribonucleic acid". Biochemistry. Nov. 22, 1983;22(24):5675-5679.

(Continued)

Primary Examiner — Jennifer Dunston
(74) Attorney, Agent, or Firm — Winston & Strawn LLP

(57) ABSTRACT

Methods for identifying ribonucleotide sequences, in vitro, using the ribosome-mediated translation, are provided.

15 Claims, 2 Drawing Sheets

(56) References Cited

OTHER PUBLICATIONS

Santoro S.W. et al. "An efficient system for the evolution of aminoacyl-tRNA synthetase specificity". Nat Biotechnol. Oct. 2002;20(10):1044-1048.
Sei-Lida et al. "Real-time monitoring of in vitro transcriptional RNA synthesis using fluorescence resonance energy transfer". Nucleic Acids Res. Jun. 5, 2000;28(12):E59.
Shimizu Y. et al. "Cell-free translation reconstituted with purified components". Nat Biotechnol. Aug. 2001;19 (8):751-755.
Surrey T. et al. "Chromophore-assisted light inactivation and self-organization of microtubules and motors". Proc Natl Acad Sci U S A. Apr. 14, 1998;95(8):4293-4298.
Sytnik et al., J. Mol. Biol. (1999), 285, 49-54.
Wolin SL. et al. "Ribosome pausing and stacking during translation of a eukaryotic mRNA". EMBO J. Nov. 1988;7 (11):3559-3569.
ISR of PCT/IL05/00540 mailed Jan. 4, 2006.
Corresponding EP 05743440 Supplementary European Search Report dated Aug. 20, 2008.
Agafonov et al., (1999) A protein residing at the subunit interface of the bacterial ribosome. Proc Natl Acad Sci U S A 96(22): 12345-9.
Agmon et al., (2003) On peptide bond formation, translocation, nascent protein progression and the regulatory properties of ribosomes. Derived on Oct. 20, 2002 at the 28th FEBS Meeting in Istanbul. Eur J Biochem 270(12): 2543-56.
Agawal et al, (2000) Visualization of tRNA Movements on the *Escherichia coli* 70s Ribosome during the Elongation Cycl. J Cell Biol 150(3):447-460.
Akhtar S and Juliano RL (1992) Cellular uptake and intracellular fate of antisense oligonucleotides. Trends Cell Biol 2(5): 139-144.
Alberts et al., (2002) Molecular Biology of the Cell, fourth edition, New York: Garland Science, p. 344.
Amann et al., (1995) Phylogenetic identification and in situ detection of individual microbial cells without cultivation. Microbiol Rev 59(1): 143-169.
Amstutz et al., (2001) In vitro display technologies: novel developments and applications. Curr Opin Biotechnol 12(4): 400-5.
Asai et al., (1999) An *Escherichia coli* strain with all chromosomal rRNA operons inactivated: complete exchange of rRNA genes between bacteria. Proc Natl Acad Sci U S A 96(5): 1971-6.
Bain et al., (1991) Site-specific incorporation of nonnatural residues during in vitro protein biosynthesis with semisynthetic aminoacyl-tRNAs. Biochemistry 30(22): 5411-5421.
Ban et al., (2000) The complete atomic structure of the large ribosomal subunit at 2.4 A resolution. Science 289(5481): 905-20.
Barhoom et al., (2011) Quantitative single cell monitoring of protein synthesis at subcellular resolution using fluorescently labeled tRNA. Nucleic Acids Res 39(19): e129.
Barhoom et al., (2013) Dicodon monitoring of protein synthesis (DiCoMPS) reveals levels of synthesis of a viral protein in single cells. Nucleic Acids Res pp. 1-10.
Baubet et al., (2000) Chimeric geen fluorescent protein-aequorin as bioluminescent Ca2+ reporters at the single-cell level. Proc Natl Acad Sci USA 97(13): 7260-7265.
Behrens et al., (2003) Is the in situ accessibility of the 16S rRNA of *Escherichia coli* for Cy3-labeled oligonucleotide probes predicted by a three-dimensional structure model of the 30S ribosomal subunit? Appl Environ Microbiol 69(8): 4935-4941.
Bevan et al., (1995) Identifying small-molecule lead compounds: the screening approach to drug discovery. Trends Biotechnol 13(3): 115-121.
Blanchard et al., (2004) tRNA selection and kinetic proofreading in translation. Nat Struct Mol Biol 11(10): 1008-1014.
Braslaysky et al., (2003) Sequence information can be obtained from single DNA molecules. Proc Natl Acad Sci USA 100(7): 3960-3964.
Campagnola and Loew (2003) Second-harmonic imaging microscopy for visualizing biomolecular arrays in cells, tissues and organisms. Nat Biotechnol 21(11): 1356-1360.
Campisi et al., (2001) Structure-based design of a dimeric RNA-peptide complex. EMBO J 20(1-2): 178-86.

Chang et al., (2006) Significance of molecular signaling for protein translation control in neurodegenerative diseases. Neurosignals 15(5): 249-258.
Cornish et al., (1994) Site-specific incorporation of biophysical probes into proteins. Proc Natl Acad Sci USA 91(8): 2910-2914.
Dahlberg et al., (1969) Electrophoretic characterization of bacterial polyribosomes in agarose-acrylamide composite gels. J Mol Biol 41(1): 139-47.
De Angelis (1999) Why FRET over genomics? Physiol Genomics 1(2): 93-99.
Deniz et al., (2000) Single-molecule protein folding: diffusion fluorescence resonance energy transfer studies of the denaturation of chymotrypsin inhibitor 2. Proc Natl Acad Sci USA 97(10): 5179-5184.
Denk et al., (1990) Two-photon laser scanning fluorescence microscopy. Science 248(4951): 73-76.
Dickson et al., (1996) Three-dimensional imaging of single molecules solvated in pores of poly(acrylamide) gels. Science 274(5289): 966-9.
Dirks et al., (2001) Methods for visualizing RNA processing and transport pathways in living cells. Histochemistry and Cell Biology 155(1): 3-11.
Dittmar et al., (2005) Selective charging of tRNA isoacceptors induced by amino-acid starvation. EMBO Rep 6(2): 151-7.
Emptage (2001) Fluorescent imaging in living systems. Curr Opin Pharmacol 1(5): 521-525.
Fuchs et al., (1998) Flow cytometric analysis of the in situ accessibility of *Escherichia coli* 16S rRNA for fluorescently labeled oligonucleotide probes. Appl Environ Microbiol 64(12): 4973-4982.
Fuchs et al., (2001) In situ accessibility of *Escherichia coli* 23S rRNA to fluorescently labeled oligonucleotide probes. Appl Environ Microbiol 67(2): 961-968.
Funatsu et al., (1995) Imaging of single fluorescent molecules and individual ATP turnovers by single myosin molecules in aqueous solution. Nature 374(6522): 555-9.
Gráf et al., (2005) Live cell spinning disk microscopy. Adv Biochem Eng Biotechnol 95: 57-75.
Green and Puglisi (1999) The ribosome revealed. Nat Struct Biol 6(11): 999-1003.
Grigoriadou et al., (2007) The tanslational fidelity function of IF3 during transition fom the 30 S intaton complex to the 70 S initiation complex. J Mol Biol 373(3): 551-61.
Gygi et al., (1999) Quantitative analysis of complex protein mixtures using isotope-coded affinity tags. Nature Biotechnology 17: 994-999.
Ha et al., (1996) Probing the interaction between two single molecules: fluorescence resonance energy transfer between a single donor and a single acceptor. Proc Natl Acad Sci USA 93(13): 6264-6268.
Ha et al., (1999) Ligand-induced conformational changes observed in single RNA molecules. Proc Natl Acad Sci U S A 96(16): 9077-9082.
Ha et al., (1999) Single-molecule fluorescence spectroscopy of enzyme conformational dynamics and cleavage mechanism. Proc Natl Acad Sci U S A 96(3): 893-8.
Hailey et al., (2002) Fluorescence resonance energy transfer using color variants of green fluorescent protein. Methods Enzymol 351: 34-49.
Hainrichson et al., (2007) Designer aminoglycosides: the race to develop improved antibiotic and compounds for the treatment of human genetic diseases. Org Biomol Chem 6(2): 227-39.
Hanes et al., (2000) Selecting and evolving functional proteins in vitro by ribosome display. Methods Enzymol 328: 404-30.
Hanley et al., (1999) An optical sectioning programmable array microscope implemented with a digital micromirror device. J Microsc 196(Pt 3): 317-331.
Heinze et al., (2000) Simultaneous two-photon excitation of distinct labels for dual-color fluorescence crosscorrelation analysis. Proc Natl Acad Sci USA 97(19): 10377-10382.
Helmchen F and Denk W (2005) Deep tissue two-photon microscopy. Nat Methods 2(12): 932-940.

(56) References Cited

OTHER PUBLICATIONS

Herzenberg et al., (2002) The history and future of the fluorescence activated cell sorter and flow cytometry: a view from Stanford. Clin Chem 48(10): 1819-27.
Huang and Cantor (1975) Studies of 30 S *Escherichia coli* ribosome reassembly using individual proteins labeled with an environmentally sensitive fluorescent probe. J Mol Biol 97(4): 423-441.
Humpher-Smith et al., (1997) Proteome research: complementarity and limitations with respect to the RNA and DNA worlds. Electrophoresis 18(8): 1217-42.
Hurlstone and Clevers (2002) T-cell factors: turn-ons and turn-offs. EMBO J 21(10): 2303-11.
Jaiswal et al., (2003) Long-term multiple color imaging of live cells using quantum dot bioconjugates. Nat Biotechnol 21 (1): 47-51.
Jenkins and Pennington (2001) Arrays for protein expression profiling: towards a viable alternative to two-dimensional gel electrophoresis? Proteomics 1(1): 13-29.
Jia et al., (1997) Nonexponential kinetics of a single tRNAPhe molecule under physiological conditons. Proc Natl Acad Sci USA 94(15): 7932-7936.
Johnson (2005) The co-translational folding and interactions of nascent protein chains: a new approach using fluorescence resonance energy transfer. FEBS Lett 579(4): 916-920.
Jovin (2003) Quantum dots finally come of age. Nat Biotechnol 21(1): 32-33.
Jun et al., (2008) Fluorescent labeling of cell-free synthesized proteins with fluorophore-conjugated methionylated tRNA derived from in vitro transcribed tRNA. J Microbiol Methods 73(3): 247-251.
Kenworthy (2001) Imaging protein-protein interactions using fluorescence resonance energy transfer microscopy. Methods 24(3): 289-296.
Klostermeier and Miller (2001) RNA conformation and folding studied with fluorescence resonance energy transfer. Methods 23(3): 240-254.
Kukhanova et al., (1974) Peptidyl-tRNA with a fluorescent label: ribosome substrates in peptide bond formation. Mol Biol Rep 1(7): 397-400.
Lafontaine and Tollervey (2001) The function and synthesis of ribosomes. Nat Rev Mol Cell Biol 2(7): 514-20.
Langlois et al., (1975) A comparison of the fluorescence of the Y base of yeast tRNA-Phe in solution and in cystals. Biochemistry 14(11): 2554-8.
Lee et al., (2010) Single-molecule four-color FRET. Angew Chem Int Ed 49: 9922-9925.
Legrain and Selig (2000) Genome-wide protein interaction maps using two-hybrid systems. FEBS Lett 480(1): 32-6.
Loy et al., (2003) probeBase: an online resource for rRNA-targeted oligonucleotide probes. Nucleic Acids Res 31(1): 514-516.
Magde et al., (1974) Fluorescence correlation spectroscopy. II. An experimental realization. Biopolymers 13(1): 29-61.
Medintz et al., (2003) Self-assembled nanoscale biosensors based on quantum dot FRET donors. Nat Mater 2(9): 630-638.
Miklos and Maleszka (2001) Protein functions and biological contexts. Proteomics 1(2): 169-78.
Muralikrishna and Cooperman (1994) A photolabile oligodeoxyribonucleotide probe of the decoding site in the small subunit of the *Escherichia coli* ribosome: identification of neighboring ribosomal components. Biochemistry 33(6): 1392-1398.
Negrutskii and Deutscher (1991) Channeling of aminoacyl-tRNA for potein synthesis in vivo. Proc Natl Acad Sci U S A 88(11): 4991-4995.
Negrutskii et al., (1994) Supramolecular organization of the mammalian translation system. Proc Natl Acad Sci U S A 91(3): 964-8.
Nilsson et al., (1997) Affinity fusion strategies for detection, purification, and immobilization of recombinant proteins. Protein Expr Purif 11(1): 1-16.
Nolkrantz et al., (2001) Electroporation of single cells and tissues with an electrolyte-filled capillary. Anal Chem 73(18): 4469-77.
Nyborg and Liljas (1998) Protein biosynthesis: structural studies of the elongation cycle. FEBS Lett 430(1-2): 95-9.

Odom et al., (1980) Distances between 3' ends of ribosomal ribonucleic acids reassembled into *Escherichia coli* ribosomes. Biochemistry 19(26): 5947-5954.
Odom et al., (1984) Relaxation time, interthiol distance, and mechanism of action of ribosomal protein S1. Arch Biochem Biophys 230(1): 178-193.
Odom et al., (1988) Fluorescence labeling and isolation of labeled RNA and ribosomal proteins. Mehods Enzymol 164: 174-187.
Olejnik et al., (2005) N-terminal labeling of proteins using initiator tRNA. Methods 36(3): 252-260.
Olliver et al., (2000) The Nucleic Acid Protocols Handbook IX 891-894.
Olofsson et al., (2003) Single-cell electroporation. Curr Opin Biotechnol 14(1): 29-34.
Palakurthi et al., (2001) Anticancer effects of thiazolidinediones are independent of peroxisome proliferator-activated receptor gamma and mediated by inhibition of translation initiation. Cancer Res 61(16): 6213-6218.
Paulsen and Witermeyer (1986) tRNA topography during translocation: steady-state and kinetic fluorescence energy-transfer studies. Biochemistry 25(10): 2749-2756.
Paulsen et al., (1983) Topological arrangement of two transfer RNAs on the ribosome. Fluroresence energy transfer measurements between A and P site-bound tRNAphe. J Mol Biol 167(2): 411-426.
Plumbridge et al., (1980) Characterisation of a new, fully active fluorescent derivative of *E. coli* tRNA Phe. Nucleic Acids Res 8(4): 827-843.
Puglisi et al., (2000) Approaching translation at atomic resolution. Nat Struct Biol 7(10): 855-61.
Ramakrishnan (2002) Ribosome structure and the mechanism of translation. Cell 108(4): 557-72.
Rathenberg et al., (2003) High-efficiency transfection of individual neurons using modified electrophysiology techniques. J Neurosci Methods 126(1): 91-8.
Recht et al., (1999) RNA sequence determinants for aminoglycoside binding to an A-site rRNA model oligonucleotide. J Mol Biol 262(4): 421-36.
Rodnina et al., (2005) Recognition and selection of tRNA in translation. FEBS Lett 579(4): 938-942.
Rosen et al., (2001) Stress-induced proteins of *Agrobacterium tumefaciens*. FEMS Microbiol Ecol 35(3): 277-285.
Ryttséne et al (2000) Characterization of single-cell electroporation by using patch-clamp and fluoescence microscopy. Biophys J 79(4): 1993-2001.
Sako and Uyemura (2002) Total internal reflection fluorescence microscopy for single-molecule imaging in living cells. Cell Struct Funct 27(5): 357-365.
Sako and Yanagida (2003) Single-molecule visualization in cell biology. Nat Rev Mol Cell Biol Suppl: SS1-SS5.
Schlegel et al., (1978) The turnover of tRNAs microinjected into animal cells. Nucleic Acids Res 5(10): 3715-3729.
Schlünzen et al., (2001) Structural basis for the interaction of antibiotics with the peptidyl transferase centre in eubacteria. Nature 413(6858): 814-21.
Schwille and Kettling (2001) Analyzing single protein molecules using optical methods. Cuff Opin Biotechnol 12(4): 382-386.
Schwille et al., (1999) Molecular dynamics in living cells observed by fluorescence correlation spectroscopy with one- and two-photon excitation. Biophys J 77(4): 2251-2265.
Shen-Orr et al., (2002) Network motifs in the transcriptional regulation network of *Escherichia coli*. Nat Genet 31(1): 64-68.
Singh et al., (1999) Rapid kinetic characterization of hammerhead ribozymes by real-time monitoring of fluorescence resonance energy transfer (FRET). RNA 5(10): 1348-1356.
Smilansky (2001) Automatic registration for images of two-dimensional protein gels. Electrophoresis 22(9): 1616-1626.
Sofia et al., (1998) Poly(ethylene oxide) Grafted to Silicon Surfaces: Grafting Density and Protein Adsorption. Macromolecules 31: 5059-5070.
Stapulionis and Deutscher (1995) A channeled tRNA cycle during mammalian protein synthesis. Proc Natl Acad Sci U S A 92(16): 7158-7161.

(56) References Cited

OTHER PUBLICATIONS

Szöllosi et al., (1998) Application of fluorescence resonance energy transfer in the clinical laboratory: routine and research. Cytometry 34(4): 159-179.

Terpe (2003) Overview of tag protein fusions: from molecular and biochemical fundamentals to commercial systems. Appl Microbiol Biotechnol 60(5): 523-533.

Thompson et al., (2002) Recent advances in fluorescence correlation spectroscopy. Curr Opin Struct Biol 12(5): 634-641.

Tsuji et al., (2000) Direct Observation of Specific Messenger RNA in a Single Living Cell under a Fluorescence Microscope. Biophysical Journal 78: 3260-3274.

Tuschl (2002) Expanding small RNA interference. Nat Biotechnol 20(5): 446-8.

van de Wetering et al., (2003) Specific inhibition of gene expression using a stably integrated, inducible small-interfering-RNA vector. EMBO Rep 4(6): 609-15.

Vanzi et al., (2003) Protein synthesis by single ribosomes. RNA 9(10): 1174-1179.

Vukojević et al., (2005) Study of molecular events in cells by fluorescence correlation spectroscopy. Cell Mol Life Sci 62(5): 535-550.

Walace (2005) The mitochondrial genome in human adaptive radiation and disease: on the road to therapeutics and performance enhancement. Gene 354: 169-80.

Washburn et al., (2001) Large-scale analysis of the yeast proteome by multidimensional protein identification technology. Nat Biotechnol 19(3): 242-7.

Watson et al., (1995) Macromolecular arrangement in the aminoacyl-tRNA.elongation factor Tu.GTP ternary complex. A fluorescence energy transfer study. Biochemistry 34(24): 7904-12.

Weiss (1999) Fluorescence spectroscopy of single biomolecules. Science 283(5408): 1676-83.

Wimberly et al., (2000) Structure of the 30S ribosomal subunit. Nature 407(6802): 327-39.

Wu et al., (2003) Immunofluorescent labeling of cancer marker Her2 and other cellular targets with semiconductor quantum dots. Nat Biotechnol 21(1): 41-6.

Yates (1998) Database searching using mass spectrometry data. Electrophoresis 19(6): 893-900.

Zhuang et al., (2000) A single-molecule study of RNA catalysis and folding. Science 288(5473): 2048-51.

Zhuang et al., (2002) Correlating structural dynamics and function in single ribozyme molecules. Science 296(5572): 1473-1476.

Zipfel et al., (2003) Nonlinear magic: multiphoton microscopy in the biosciences. Nat Biotechnol 21(11): 1369-1377.

Zlokarnik et al., (1998) Quantitation of transcription and clonal selection of single living cells with beta-lactamase as reporter. Science 279(5437): 84-8.

\* cited by examiner 210  220                                              230

301. VGSDKCTTIHYNYMCNRSSCMGQLKKWVDSTPKPPGT
     RVRKAMAIYQSRRQHMTEVVSVTKCTYSPALNVQLVK
     ESGGGRLVQPGGSLR (SEQ ID NO. 1)

302. SCAASGYTFTNYGMNWVRQQDQPMREEEEVETFAFQA
     EIAQLMSLIINTFYSNKEIFLRENSSDALDKTIAKSG
     TKAFME (SEQ ID NO. 2)

303. KRKKKRRKRRKK (SEQ ID NO. 3)

304. RKRRKKK (SEQ ID NO. 4)

METHODS FOR EVALUATING RIBONUCLEOTIDE SEQUENCES

CROSS REFERENCE TO RELATED APPLICATIONS

This application is a 35 U.S.C. §371 filing of International Application No. PCT/IL2005/000540, filed May 26, 2005 and published, in English, as International Publication No. WO 2005/116252 A2 on Dec. 8, 2005, and claims priority of U.S. Provisional Application No. 60/574,210 filed May 26, 2004, which applications are hereby incorporated herein, in their entirety.

FIELD OF THE INVENTION

The present invention relates to methods for identifying ribonucleotide sequences by monitoring ribosomal translation, in vitro.

BACKGROUND OF THE INVENTION

RNA reading has an important value in biological and pharmaceutical industries. Identifying expression levels of multiple genes between various biological samples enables to perform genotyping, study disease pathways and obtain improved diagnosis and prognosis of diseases among other applications.

Since the early 1990s, the simultaneous measure of the expression of thousands of different RNA gene products in a biological sample, such as a cell lysate, became feasible by the introduction of DNA microarrays (DNA chips). A DNA chip consists of numerous addressable locations. In each location numerous copies of a specific single strand DNA molecule (probes) are attached. When a sample containing a DNA strand that is complementary to one or more of the DNA molecules on the chip, hybridization takes place. With appropriate sample labeling strategies, a pattern indicating the identity of the DNA strands and their amounts is obtained. The chip with its large number of probes can identify, quantitate and compare the RNA sequences expressed in a set of samples (e.g. Nature Genetics, January 1999 Supplement).

The technology of DNA chips has several major drawbacks: design and production of chips is lengthy and expensive; assay performance takes several days and may include biased intermediate stages such as amplification; inaccurate quantitation and insensitivity to mRNA isoforms. The most prominent drawback of these methods is that they allow only partial analysis of gene products. In the case of oligo chips, only a predetermined oligo sequence designed for that chip can be detected. In the case of cDNA chips, the content of the chip is obtained by 'trial and error' and hence gene coverage is not guarantied. Moreover, any attempt to analyze hundreds of thousands of RNA isoforms would result in impractical chip density which would not enable to distinguish between RNA variants and isoforms. In addition, commercial off the shelf chips usually encompass well-known, recognized genes and thus analysis is limited to identification of such already well-known genes. Non-adequate evaluation of expression magnitude is another disadvantage of the commercial chips as it is common to have several spots that putatively cover the same gene, and show gross differences in expression estimates, sometimes of a factor of 3 or more.

A protein synthesis monitoring (also termed hereinafter "PSM") system and methods of using same is disclosed by the inventor of the present invention in International Patent Application No. PCT/IL03/01011, Publication No. WO2004/050825, which is incorporated here in its entirety. PSM includes a plurality of markers, each marker encompasses a pair of interacting labeling moieties, the first moiety being attached to a ribosome or a fragment thereof and the second moiety being attached to one of the following entities: the ribosome or the fragment thereof, tRNA or amino acid. Protein synthesis in PSM is carried out by monitoring the signal sequences generated upon excitation of the markers. WO2004/050825 discloses that using the PSM system enables real-time monitoring of proteins synthesis in vivo and further allow identifying the amino-acid sequences of the protein being synthesized through database interrogation process.

U.S. Pat. No. 5,706,498 discloses a gene database retrieval system for retrieving gene sequences having a sequence similar to a sequence data from the gene database. The system is capable of storing the sequence data of genes whose structures or sequences were analyzed and identified. The system includes a dynamic programming operation unit for determining the degree of similarity between target data and key data by utilizing the sequence data of the bases of the gene from the gene database as the target data and the sequence data of the bases as the key for retrieval, and further contains a central processing device unit for allowing access to the gene database in parallel to the operation process for determining the degree of similarity. U.S. Pat. No. 5,706,498 merely provides a database retrieval tool in silico but does not teach or even suggest identification of mRNA molecules in cellular systems.

U.S. Pat. No. 5,856,928 discloses a system for characterizing and interpreting nucleotide and amino acid sequences. Natural numbers are assigned to represent DNA and mRNA nucleotide bases (n-numbers 0, 1, 2, 3), base pairing numbers in RNA (p-numbers 0, 1, 2, 3), and amino acids in protein (z-numbers with seventeen prime numbers and odd numbers 1, 25, 45; all smaller than 64). Gene and protein sequences may be represented, characterized and interpreted by their specific n-sums and z-sums. The system disclosed in U.S. Pat. No. 5,856,928 is in fact a representational scheme facilitating computation and characterization of nucleotide and amino acid sequences in silico. This system cannot provide mRNA identification in cellular systems.

Nowhere in the background art is it taught or suggested that mRNA may be identified by utilizing the putative transcription activity. Moreover, there is an unmet need to measure RNA through its natural role, namely as a template for protein production, rather than through reverse transcription followed and/or hybridization techniques.

SUMMARY OF THE INVENTION

The present invention provides methods for identifying the ribonucleotide sequences of mRNA molecules. The method of the present invention is essentially different from any other method known in the art for mRNA identification as it uses the cellular translation mechanism which is carried out by ribosomes for identifying the RNA molecules being used by this mechanism as a template for protein translation. Thus, the method of the invention is devoid of the drawbacks characterizing the methods known in the art. Particularly, the methods of the invention do not require use of DNA chips and thus the entire stage of chip design is avoided. Moreover, RNA identification according to the methods of the present invention does not require reverse transcription, amplification or fluorescent labeling. Another advantage of RNA identification according to the methods of the present invention over methods known in the art is that the fundamental components of the PSM system, namely a solid substrate such as a microscope slide with ribosomes immobilized thereto and a cell-free translation system, are readily accessible and can be adjusted for any assay and biologic source.

In the disclosed method, RNA is fed into a cell-free translation system, also termed hereinafter PSM system, where ribosomes are immobilized on a solid substrate, for example, a microscope slide. PSM systems, disclosed in WO2004/050825, enables to perform a PSM assay which includes monitoring protein synthesis through detection of the signal sequences produced by fluorescent markers being attached to ribosomes or fragments thereof, amino acids and tRNAs. The signal sequences are generated in the PSM system upon excitation of the fluorescent markers. mRNA molecules that correspond to signal sequences obtained in the PSM assay may be identified by performing database interrogation in a database, termed hereinafter "PSM database". The PSM database is specifically designed for the method of the invention and comprises a plurality of signal sequences or the corresponding data streams wherein each signal sequence is assigned to a particular RNA molecule.

The method of the present invention is particularly advantageous over other methods known in the art for mRNA identification since mRNA is monitored substantially throughout its length, thus facilitating to distinguish between variants and isoforms of the same generic RNA molecule.

Moreover, using the methods of the present invention RNA molecules are detected at a resolution of a single RNA molecule, thereby the number of RNA molecules processed in the PSM assay can be calculated. Thus, the methods of the invention provide analysis on single molecule basis, hence providing an ultimate signal to noise ratios. Additionally, RNA identification according to the method of the present invention is carried out in real time substantially during elongation of the RNA molecules. Thus, using the method of the invention the RNA sequence enables discrimination between isoforms. In addition, the entire identification assay carried out by the method of the present invention is completed within hours rather than days.

According to one aspect, the present invention provides a method for RNA identification comprising:
(a) providing a PSM system, wherein the PSM system comprises:
 (i) at least one marker detectable through detection of electromagnetic radiation, the at least one marker comprising a pair of interacting labeling moieties, wherein the first moiety being bound to a ribosome or a fragment thereof, the ribosome or the fragment thereof being attached to a solid substrate, and the second moiety being bound to an entity selected from the group consisting of: the ribosome or the labeled fragment thereof, tRNA and amino acid, wherein the marker is capable of emitting electromagnetic radiation in response to translation activity;
 (ii) at least one translation component selected from the group consisting of: aminoacyl-tRNA synthetases, initiation factors, elongation factors, termination factors, energy sources and energy regenerating molecules; and
 (iii) detection means adapted to measure emitted radiation from the PSM system;
(b) introducing at least one RNA molecule into the PSM system: and
(c) detecting electromagnetic radiation signals obtained in response to translation activity.

According to one embodiment, the PSM system comprises a plurality of markers. According to another embodiment, the method comprises introducing a plurality of RNA molecules into the PSM system.

According to another embodiment, the solid substrate is selected from the group consisting of: glass, glass slide adapted for microscope means and a solid substrate having a mica surface.

According to yet another embodiment, the method further comprises identifying the ribonucleotide sequence of the at least one RNA molecule.

According to another embodiment, the step of identifying the ribonucleotide sequence of the at least one RNA molecule comprises:
 performing PSM database interrogation, thereby assigning said at least one signal sequence to at least one particular RNA molecule.

According to yet another embodiment, identifying the ribonucleotide sequence of at least one RNA molecule further comprises storing the at least one signal sequence in a PSM database.

According to yet another embodiment, the step of performing PSM database interrogation comprises:
 determining the probability of an RNA molecule in the PSM database to produce said at least one signal sequence; and
 selecting one or more RNA molecules having the highest probabilities thereby assigning the one or more RNA molecules to said at least one signal sequence.

According to yet another embodiment, the at least one signal sequence is composed of one or more values selected from the group consisting of: time, spatial coordinates, signal type and signal intensity.

According to yet another embodiment, signals are obtained by energy transfer between the pair of interacting labeling moieties. According to yet another embodiment, the signals are selected from the group consisting of: FRET signals, quenching signals and a fluorescent signals.

According to yet another embodiment, the marker comprises a label selected from the group consisting of: a fluorescent dye, a fluorescent amino acid, a fluorescent peptide or protein, a fluorescent nucleotide, a quantum dot, a luminescent substance, a donor-quencher pair and a fluorescent donor-acceptor pair. According to yet another embodiment, the second labeling moiety is a fluorescent amino acid.

According to yet another embodiment, the ribosomal fragment is selected from the group consisting of: ribosomal RNA, a ribosomal protein, ribosomal protein L1, ribosomal protein L11, ribosomal protein S1 and fragments thereof. According to an alternative embodiment, the ribosomal fragment is located near a ribosomal site selected from the group consisting of: ribosomal A site, ribosomal P site, ribosomal E site, peptide exit channel site, L1 arm, and L7/L12 arm.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION

Figure 1:
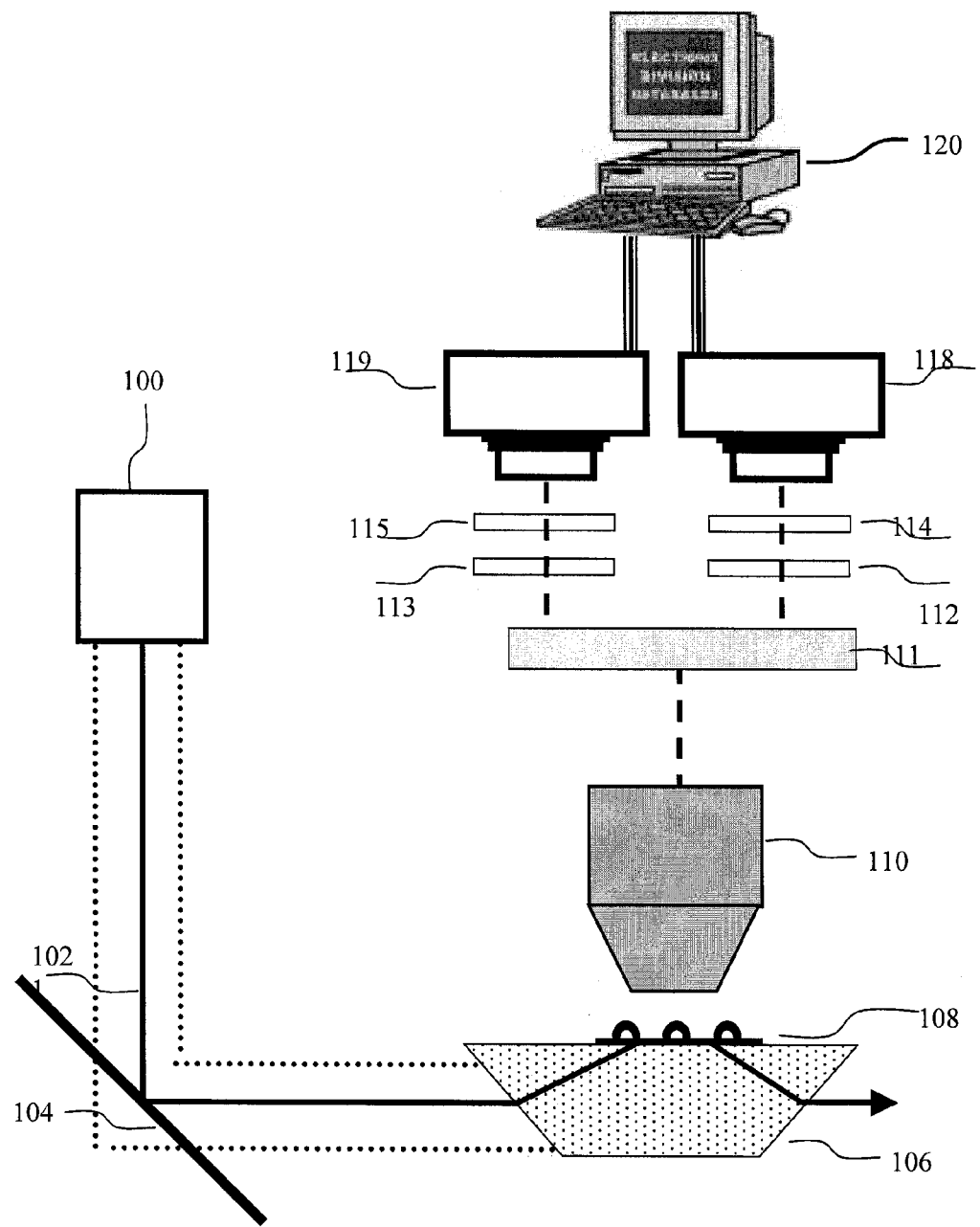
FIG. 1 describes a general embodiment of the system with TIR illumination and optical setup for double labeling.

The present invention provides a method for RNA identification, preferably by feeding the RNA into an in-vitro protein synthesis monitoring system, also termed hereinafter "PSM system", and determining the identity of the RNA by monitoring translation activity at the PSM system.

The terms "RNA" and "mRNA" are interchangeably used herein to describe a ribonucleotide sequence that transfers genetic information to ribosomes, where it serves as a template for protein synthesis. A ribonucleotide sequence is a polymer of ribonucleic acids, and is a constituent of all living cells and many viruses. It consists of a long, usually single-stranded chain of alternating phosphate and ribose units with the bases adenine, guanine, cytosine, and uracil bonded to the ribose. The structure and base sequence of RNA are determinants of protein synthesis and the transmission of genetic information.

The term "in-vitro" as used herein, refers to cellular systems rather than in silico systems. In a particular embodiment, in vitro is used to define a cell-free system comprising ribosome(s) and components required for carrying out translation in the ribosome(s) of the system. However, in vitro as used herein may also refer to a cellular system with the proviso that such system would enable RNA identification by PSM assay in accordance with the teaching of the present invention.

The term "translation activity" as used herein refers to any step during the transition from mRNA to an amino acid or an amino acid sequence, including, but not limited to, mRNA-tRNA recognition and pairing (also known as codon-anti codon paring), amino acid activation (or tRNA aminoacylation), attachment of an amino acid to the tRNA and addition of the amino acid to a growing peptide chain.

The background art merely teaches how to identify RNA molecules by using its propensity for hybridization, and does not consider or suggest using its natural role as a template for protein synthesis. The background art suffers from severe disadvantages such as the need for elaborate chip design, ambiguous results, complex and lengthy result analysis, insensitivity to RNA isoforms, inaccurate quantitation and lengthy assay preparation. A comprehensive review on DNA chips is provided in the supplemental issue of Nature published January 1999. Additional publications are available from commercial suppliers such as Affymetrix, Agilent, and Amersham Pharmacia.

In principle, the probes contained within DNA chips (or microarrays) are broadly divided into two categories: oligonucleotides and cDNAs. In the first category, the strands are relatively short (20-70 base pairs). They are synthesized either directly on the chip or in a solution and subsequently printed. cDNA strands are usually longer, often between 200-1000 base pairs, and they are produced by techniques of genetic engineering (or cloning) from living cells.

In oligo microarrays, the chip is carefully designed and the content of each spot is well defined. Because of the relatively short sequence length, several oligos are required to properly identify a gene. Identification of hybridized mRNAs is complicated in cases where one gene gives rise to several different mRNAs (as in the event of alternative splicing). Further, hybridization signals tend to fluctuate, yielding relatively low signal to noise. Due to these obstacles, the designing of an oligo microarray is a difficult, costly and time-consuming process.

In cDNA microarrays, chip content commonly arises from a gene library. There is no assurance that the cDNAs on the chip cover all genes of interest, neither is there any assurance of uniqueness. Repetitive sequences, as well as sequences common to several gene families, can lead to cross-hybridization. In fact chip content is often unknown until after the assay is analyzed, as cDNA sequencing is expensive and thus performed only for spots of interest. There are serious quality control problems involved with cDNA chips, such as variation in the concentration of the probes on a slide, incorrect identity of some probes due to mis-annotation, cross-hybridization of splice-variants, differences in the probe length, pin-to-pin variation and spot size variation.

Preparation of a DNA Chip May Last Several Weeks and Even Several Months, depending on the type of chip, number of genes and the required precision. In the case of oligo chips, off-the-shelf chips or oligo libraries ready for printing can be purchased. Performance of the analysis usually takes a few days. The stages typically involve harvesting total RNA from a single cell or from a plurality of cells; applying reverse transcription thereby obtaining cDNA; optionally amplifying the resulting products, either through bacterial growth or through PCR; fluorescent labeling and hybridization to the chip and finally the chip is scanned and the results analyzed.

The present invention overcomes the disadvantages of background art by providing a method for RNA identification, preferably by feeding the RNA into an in-vitro protein synthesis system, and determining the identity of the mRNA being translated by monitoring the synthesis process.

In order to better describe the disclosure, the technology of protein synthesis monitoring (PSM) will be now briefly explained. This technology with its applications is described in detail in WO2004/050825, hereby incorporated by reference as if fully set forth herein. In PSM, use is made of the physical phenomenon of FRET (fluorescence resonance energy transfer). A donor fluorophore and a matching acceptor fluorophore are selected so that the emission spectrum of the donor overlaps the excitation spectrum of the acceptor. When donor and acceptor are in close proximity (usually less than 10 nm), excitation of the donor will cause emission from the acceptor, as some of the energy passes from donor to acceptor via a quantum coupling effect. Thus, donor and acceptor serve as a proximity gauge: when they are near, a FRET signal can be generated, and when they are not, a FRET signal cannot be generated. In practice, a ribosome is engineered to carry a donor fluorophore, and tRNA and/or amino acids and/or some other part of the ribosome are either engineered to carry acceptor fluorophores or else their natural fluorescent properties are utilized as acceptors. The PSM assay involves translation of a pool of RNA molecules in vitro or in vivo using ribosomes tRNA and amino acid molecules. In order to monitor the translation, a light source illuminates the ribosomes thus exciting the donor fluorophores and thereby the acceptor fluorophores whenever these components are in sufficient proximity to each other. The resulting signals are detected and optionally stored. Using data base interrogation, the protein being synthesized is identified.

According to WO2004/050825, PSM uses the FRET effect to monitor the synthesis process performed by a ribosome, and identify the protein being synthesized, substantially in real time. Various labeling strategies can be used for PSM. In one preferred embodiment, the ribosome is labeled with donor and one or more amino acid species are labeled with acceptor fluorophore. According to certain embodiments, all amino acid species are labeled. When a labeled amino acid is processed by the ribosome, a FRET signal is generated. The resulting signal sequence corresponds to the loci of labeled amino acids within the protein sequence, and therefore is a characteristic of this protein and enables its identification.

Other labeling strategies involve labeling tRNA rather than amino acids; labeling both donor and acceptor on selected parts of the ribosome; labeling with more than one type of FRET pair; labeling all amino acids and/or all tRNAs; and many other variants of the basic idea. Some of these variants are discussed below while many others will be evident to anyone skilled in the appropriate art.

Thus, according to one aspect the present invention provides a method for RNA identification the method comprising:
(a) providing a PSM system;
(b) introducing at least one RNA molecule into the PSM system; and
(c) detecting electromagnetic radiation signals obtained in response to translation activity; and optionally
(d) identifying the ribonucleotide sequence of the at least one RNA molecule.

One exemplary flow of operation according to the aspect of the invention is now described. An optical apparatus monitors the protein synthesis system (PSM), described hereinabove and in WO2004/050825, optionally by directing electromagnetic radiation of the required wavelength and energy onto the marked system, thereby exciting the donor fluorophores. The acceptor fluorophores on the tRNAs and/or amino acids and/or on the ribosome respond to this energy with the FRET signal whenever a donor and acceptor pair are in sufficient proximity, indicative of particular steps of translation activity, for example, indicating the incorporation of a particular tRNA or amino acid by said synthesis system. Fluorescence radiation emitted from acceptor fluorophores is detected by the optical apparatus and the event is recorded by the image acquisition device connected to a computerized analysis unit. The acquired image sequence is then analyzed by the software for the purpose of identifying the mRNA(s) associated with the recorded translation activity.

Analysis includes separation of the initial signals (for example as a stream of video frames) into a set of signal sequences, wherein each signal sequence is emitted from a single ribosome. Each ribosomal signal sequence is separately analyzed to identify the mRNA that served as a template for its synthesis. Alternatively, the mRNA that served as a template for the recorded synthesis is analyzed directly by interrogating the signal sequence in a PSM databases which includes signal sequence data associated with RNA rather than with proteins.

Optionally, a signal sequence data obtained from the PSM assay is stored in the PSM database. The correspondence between the data in the PSM database and the RNA molecules assigned thereto depends on the labeling strategy used in the PSM assay. Several labeling strategies are detailed below. The resulting sequence of detection events is a characteristic of the RNA used as a template for the protein synthesis. This signal sequence may be described as a bit stream with zeroes and ones (as commonly used to describe data in computer science terminology). This stream may contain some uncertainty as to the number of bits in each field, as well as other elements of uncertainty.

The signal is subsequently used to interrogate a database of signals computed in silico from a relevant database of protein or nucleotide sequences. The method disclosed herein uses this signal to identify the mRNA that most likely produced the signal. In the event that for a particular RNA molecule only part of the elongation and/or translation event is recorded, then the resulting signal sequence does not correspond directly to the RNA. However, the PSM database includes information relating to the labeling strategy and to various translation events and therefore can assign any signal sequence to an RNA molecule even if the signal sequence does not include record of the entire translation event.

In the present invention, ribosomes are immobilized on a solid substrate. Numerous solid substrates are suitable for carrying out the method of the invention providing that the surface enables to immobilize ribosomes thereto and allows the immobilized ribosome to execute translation activity in the cell-free translation system. Solid substrates that may be utilized for immobilizing ribosomes are known in the art (see for example Ha, T, *Single-molecule fluorescence resonance energy transfer*, METHODS 25, 78-86 (2001)).

According to certain embodiments, the solid surface is adapted for use under a microscope, thereby enabling to monitor the translation activity through the microscope. Preferably, the microscope as well as any monitoring means that is utilized in the context of the present invention is adapted for detecting single molecule fluorescence. According to some embodiment, the detected activity is stored.

Preferably, ribosomes are immobilized at a density that permits optical resolution at the level of a single ribosome. The ribosomes are labeled with one or more types of donor fluorophores, and either some tRNA species, or some amino acid species, or another part of that ribosome, or a combination thereof, labeled with acceptor fluorophores that match the donor(s). The donor-acceptor pair is also referred herein as the first and second labeling moieties of the marker used in the PSM assay. In other preferred embodiments assignment of donors and acceptors to molecules could be switched. Next, the sample containing the mixture of mRNA molecules to be assayed is introduced with the other components required for performing translation in a cell-free system including tRNAs, labeled and unlabeled; synthetases; initiation, elongation and termination factors energy sources (ATP, GTP), energy regenerating systems (creatine phosphate and creatine phosphokinase for eukaryotic systems (Shimizu et al, *Cell-free translation reconstituted with purified components*. Nat. Biotechnol. 2001, 19(8):751-5). The entire translation system is placed under a microscope equipped for single molecule detection, such as instruments available from Zeiss (Oberkochen, Germany) and Leica (Wetzlar, Germany), with an image acquisition device operable at a sufficient rate (10-100 frames per second), and computational units that can acquire and analyze the resulting images and data.

The marker optionally comprises at least one photoactive component. The emitted electromagnetic radiation is detected and can be analyzed to identify and measure RNA molecules in a sample mixture. The procedure can optionally be performed simultaneously for hundreds, thousands and even millions of single ribosomes.

The method of the invention may be carried out in accordance with the following alternatives:

tRNA labeling. In this embodiment the acceptor fluorphore or fluorophores are attached to one or more species of tRNA. Methods of labeling tRNA are discussed in detail in WO2004/050825, previously incorporated by reference.

Amino acid labeling. Amino acid labeling is preferable for measuring RNA in vitro (more preferable than it is for in-vivo applications of PSM) since proper structure, folding and functionality of the synthesized protein is not crucial. In addition, amino acid labeling is relatively straightforward.

Double labeling. According to an alternative embodiment, more than one FRET pair is utilized thereby distinct tRNAs or amino acids being attached to distinct labeling moieties. For example, two donors with distinct emission spectra are placed on one ribosome, and matching fluorescent acceptors can be attached to tRNAs or to amino acids. For example, an arginine tRNA is labeled with an acceptor of one color, and a lysine tRNA is labeled with an acceptor of a different color. The appropriate pair of donors is attached to, for example, ribosomal proteins L1 and S1, respectively. This scheme is beneficial even if only two out of the 20 amino acids are labeled, since the identification of the mRNA being translated in this setting depends on the interspersion profile of one amino acid relative to the other, rather than on the timing of the FRET signals. This removes the dependence of the identification process on temporal aspects of the synthesis, such as codon bias, variable tRNA species abundance, effects of RNA secondary structure (Pelletier J, Sonenberg N. The involvement of mRNA secondary structure in protein synthesis. Biochem Cell Biol. 1987, 65:576-581), ribosome pausing (Wolin S L and Walter P., EMBO J. 1988, 7:3559-3569), among other aspects of synthesis. In another preferred embodiment, the two spectrally distinct acceptors are selected to respond to a single donor.

Full sequence labeling. This scheme calls for labeling the ribosome with one, two or more donors with distinct emission spectra, and labeling the entire set of amino acids and/or tRNAs with acceptors of corresponding excitation spectra. This strategy is in contrast to labeling with only one FRET pair, where one subset of amino acids is labeled and the complementary subset remains unlabeled, in order to produce an informative signal sequence. Such full sequence labeling allows the sequence of amino acids to be read in its entirety, obviating the need for estimating the numbers of consecutive unlabeled events (see WO2004/050825 for section entitled "Data interpretation simulation"). As in the strategy of double labeling described above, full sequence labeling is independent from temporal aspects of the synthesis. Full sequence labeling also offers important additional advantages, such as the possibility of identifying mutations, and that of identifying mRNAs from a given organism based on an mRNA database of another (similar) organism, based on sequence matching.

Identifying the ribonucleotide sequence of the at least one RNA molecule, using PSM assay according to the principles of the present invention, comprises:
  performing PSM database interrogation, thereby retrieving one or more PSM signal sequences corresponding to one or more ribonucleotide sequences from the PSM database that conforms with said at least one signal sequence, thereby assigning said at least one signal sequence to at least one particular RNA molecule.

The identification process may further includes, prior to database interrogation any one of the following steps:
  a) transferring the signals to a computerized analysis station; and/or
  b) clustering said signals into a list of signal sequences, the list comprises at least one signal sequence wherein the at least one signal sequence corresponds to signals obtained from a single ribosome; and/or
  c) transforming the at least one signal sequence into at least one data stream.

In order to identify a proteins or RNA molecules from PSM signal sequence, the signal sequence data obtained during PSM assay must be processed and compiled to enable such identification. In order to allow efficient and accurate identification, the following general three steps must be taken: (i) modeling of the data obtained from the PSM process; (ii) construction of a scoring function; and (iii) performance of efficient and accurate classification of the modeled data. The term "scoring function" as used herein refers to an estimate of the probability that a given signal sequence obtained from a PSM assay corresponds to a particular ribonucleotide sequence or subsequence. This probability is in effect the probability that a specific ribonucleotide sequence or subsequence, the details of which are stored in the PSM database, would yield a signal sequence that is substantially identical to said signal sequence obtained from the PSM assay. A value obtained from the scoring function is not necessarily identical to the probability value. In fact, it may be difficult or even impossible to compute said probability value with sufficient precision. However, for the purpose of prioritizing and/or determining the best RNA candidates, stored in the database, that are the plausible generators of the measured signal, the value yielded by the scoring function may provide sufficient information.

I. Modeling the Data Obtained from the PSM Process

In the modeling step, the physical and chemical events leading to the production of the PSM signal sequence are modeled, as precisely as possible, by computerized algorithms. Such an algorithm produces, from a ribonucleotide sequence (or a protein sequence), an expected PSM signal sequence that is stored in the PSM database.

In modeling the PSM process, as much as possible information about the factors effecting the production of the PSM signals needs to be known. The most important factors are labeling strategy and translation mechanism characteristics. Accordingly, a signal sequence is commonly of the form $S=(t1, x1, y1, s1), (t2, x2, y2, s2), \ldots, (tn, xn, yn, sn), \ldots$. Where $t_i$ denotes a timing value, $x_i$ and $y_i$ denote image coordinates, and $s_i$ denotes signal type or intensity (of both donor and acceptor). A signal sequence obtained during PSM assay is recorded and forwarded to a software module (also termed a "sequence analyzer") which transforms the sequences into one or more data-stream of FRET on/off signals, as described in detail in WO2004/050825.

Preferably, every stretch of length K of a protein or an RNA sequence is modeled, where the number K depends on the labeling strategy used in the PSM assay and additional factors. If, for example, K=100 then an mRNA with 300 codons will have 200 entries in the database, one for each subsequence of length 100. The reason for this indexing is that it is impossible to determine that the synthesis process is recorded right from its initiation. However, the modeling algorithm is directed to identify an mRNA even if the ribosome is monitored only during part of the translation period. The following labeling strategies are used in a PSM assay of the present invention:

1. Labeling of all Amino Acids with 20 Distinct Colors.

Though this may introduce technical complexity it is relatively easy to analyze the resulting signal in silico using bioinformatic techniques. The mRNA sequence is identical to the labeled sequence, and no modeling is required. The scoring function can be simply based upon the familiar BLAST algorithm.

2. Labeling of all Amino Acids or tRNAs with 2 Distinct Colors

This case is very similar to the previous one, except that instead of 20 or more colors we obtain a binary sequence with only two types of colors. In the modelling, the same process is repeated, transforming the sequence into a binary sequence. Again, the BLAST algorithm can be used for scoring.

3. Double Labeling of Two Amino Acids or tRNAs with 2 Distinct Colors

This case is very similar to the previous two, the difference being that most amino acids (or tRNAs) are disregarded, leaving a labeled binary subsequence of the original, full sequence. In the modelling, the same process is repeated, transforming the sequence into a binary sequence with only the labeled tRNAs accounted for. Again, the BLAST algorithm can be used for scoring.

4. Single Labeling of Several Amino Acids or tRNAs with a Single Color

In this scenario, only a single label is used. Thus, the amino acid (or tRNA) sequence is partitioned into two types—labeled versus unlabeled. The signals obtained are interspersed with "no signals". Thus, the data stream of PSM signals measured from a single ribosome consists of a list of temporal data, indicating the precise time measurement at signal detection: t1, t2, t3, and so on. We can call this time sequence the timing fingerprint of an mRNA. In the database, we need to be able to compute the timing fingerprint for each mRNA in the database. For this, we need to measure the timing fingerprints for a sufficient number of mRNA species, and from these measurements deduce the correct model. For example, we can measure the timing fingerprints for mRNAs which are polymers of a single codon, or a single tRNA, and thereby deduce the average and standard deviation of timing for incorporation of that particular tRNA or amino acid. Once the model is available, we can compile a database of timing fingerprints for each of the mRNAs in the PSM mRNA database.

In this setting, the scoring function that should be used is based on the description above, where the comparison between a measured timing fingerprint and a candidate timing fingerprint from the database is based on evaluation of the probability that the candidate mRNA actually yielded the measured timing fingerprint, based on the statistical measurements made while constructing the database.

II. Construction of a Scoring Function

Upon production of a set of expected sequences corresponding to a set of mRNA molecules of interest and storage of this set, a scoring function is applied. The scoring function provides the probability (p-value) for a particular signal sequence stored in the PSM database to yield the signal sequence measure by the PSM assay. Thus, for each entry in the PSM database, the probability of matching to the measured PSM signal sequence obtained during PSM assay is computed. As a result of such computation, the most probable matches are selected. The signal sequence obtained during PSM assay is assigned to the RNA molecules corresponding to the most probable matches.

For the purpose of scoring, the degree of similarity between the signals produced during the PSM assay and the signals stored in the PSM database can be calculated using the system disclosed in U.S. Pat. No. 5,706,498. This patent discloses a database retrieval system adapted for determining the degree of similarity between target data and key data.

III. Performance of Efficient and Accurate Classification of the Modeled Data.

The database and scoring function described above, need to be efficiently arranged in order to enable quick and efficient analysis. Database arrangements are discussed in detail in numerous prior art documents, such as for example Donald E. Knuth, The Art of Computer Programming, Addison-Wesley.

U.S. Pat. No. 6,189,013 discloses a relational database system for storing biomolecular sequence information in a manner that allows sequences to be catalogued and searched according to association with one or more projects for obtaining full-length biomolecular sequences from shorter sequences.

Numerous applications of RNA measurement are currently practiced while others are attempted or will become practicable in the next few years. Reviews of current and foreseen applications for RNA reading devices can be found in the following market research reports: DNA Microarrays and Their Materials, published in January 2004 by Business Communications Company Inc of Norwalk, Conn.; DNA Probes-based Diagnostics, published in January 2002 by Global Industry Analysts, Inc, of San Jose, Calif.; Outlook for DNA Microarrays: Emerging Applications and Insights on Optimizing Microarray Studies, published in January 2002 by the Cambridge Healthtec Institute of Newton Upper Falls, Mass. In addition, discussion of major applications can be found in the scientific literature. For example, use of DNA chips for diagnosis and prognosis is discussed in Ken Garber, Science, 303:1754-1755, 2004; use of DNA chips for SNP analysis is discussed in Erdogan F, et al., Nucleic Acids Res. 2001, 29:E36. The term "SNP" refers to a single nucleotide polymorphism, a mutation involving a single base.

Illustrative, optional methods for monitoring protein synthesis are now described in detail below. The method will be described in selected variants and applications by way of an example, and it should be recognized that the illustrated embodiments should not be taken as a limitation on the scope of the disclosure. Some, but not all of the variants of the invention not mentioned here are: using a different type of microscope or illumination; using a different fluorescent labeling scheme or strategy; Attaching fluorophores to other ribosomal proteins or locations, or using alternative labeling protocols; using other types of fluorophores, such as organic dyes, fluorescent proteins such as GFP or any of its variants; using a different data analysis method and system; using a different substrate for ribosome immobilization or a different strategy for viewing functioning ribosomes.

EXAMPLES

Example 1

RNA Identification with Two Donors and Amino-Acid Labeling

FIG. 1 describes one optional but preferred embodiment for an exemplary apparatus for data acquisition, based on a wide-field microscope equipped with TIR (Total internal reflection, a microscopy illumination method that illuminates a volume at the interface of two materials with different refractive indices) illumination and intensified CCD camera. This setup is useful for in-vitro single-molecule protein synthesis monitoring application, where the ribosomes are immobilized on the microscope slide.

In this preferred embodiment the ribosome is labeled with one or two quantum dots as fluorescent donors. A ribosomal protein, such as optionally and preferably L1, is first biotinylated using FluoReporter Biotin-XX protein labeling kit (Molecular Probes, cat# F-2610) according to manufacturer protocol. Then, the biotinylated protein is linked to Qdot™ 525 Streptavidin Conjugate (QuantumDot) according to manufacturer protocol. In a similar way, a second ribosomal protein, such as optionally and preferably S1, is labeled with Qdot™ 605 Streptavidin Conjugate. Then, a fluorescent acceptor with excitation maximum near 525 nm is attached to one amino acid, in this example lysine, and a fluorescent acceptor with excitation maximum near 605 nm is attached to the other amino acid, in this example arginine (see below for techniques of amino acid labeling). For the convenience of the ensuing discussion the appearance of the emission from the lysine acceptor is termed "green" and the emission of the arginine acceptor is termed "red".

The two-color labeling scheme has an advantage over one-color labeling, even if only two amino acids are labeled as the identification of the mRNA being translated depends on the interspersion profile of one amino acid relative to the other, and not solely on the temporal sequence of events. This is explained in more detail below. Double labeling also removes the dependence on temporal aspects of synthesis that affect the synthesis rate, as discussed above.

Referring to FIG. 1, laser 100 is a diode-pumped doubled YAG laser (Crystalaser, Reno, Nev.) that can excite a wide range of dyes. Laser illumination 102 travels through a dichroic mirror 104 (Chroma Technology, Brattleboro, Vt.) and into a dove prism 106 such as a small Pellin Broca prism (CVI laser) where the illumination undergoes TIR. The prism is optically coupled to the fused silica bottom of the sample chamber 108, so that evanescent waves illuminate up to 150 nm above the surface of the fused silica, thereby illuminating the immobilized ribosomes. The emitted fluorescence signals (both donors and acceptors) pass through objective 110 (Olympus, DPLanApo 100 UV 1.3 oil, or PLAPO60XO, Plan APO 60x oil immersion, NA=1.4 working distance=0.15 mm), through a dichroic splitting filter 111 (Chroma Technology, Brattleboro, Vt.) which splits the image into green (112, 114, 118) and red (113, 115, 119) channels. In each of the channels the emitted signals pass through fluorescent filters (112 and 113), through imaging lenses (114 and 115) into intensified CCD (ICCD) cameras 118 and 119 such as Cascade:512B available from Roper Scientific Photometrics. The readout from both cameras is transferred digitally to computer system 120 for image analysis, signal processing and subsequent identification of the mRNA being translated.

The ribosomes are immobilized on the microscope slide. The slide may have a mica surface (Novascan Techniques™) which is transparent and flat on a molecular size scale. Ribosomes, either labeled or unlabeled, undergo binding to mica in a few seconds, allowing the detection of single fluorescence images in aqueous buffer. A large excess of ribosomes and a short incubation period are employed for single molecule detection. Mica-bound ribosomes retain their activities, as shown in Sytnik et al., J. Mol. Biol. (1999), 285, 49-54, where detailed protocols are provided. Ribosomes can also be immobilized on surface treated glass slides. Ribosomes should be immobilized at a density that permits optical resolution of single ribosomes. For example, a minimal distance of 1-2 microns could be kept between ribosomes.

As a ribosome processes the mRNA template, electromagnetic radiation of the appropriate wavelength is used to simultaneously excite the two types of donors. This is possible since quantum dots have a wide excitation range, but narrow and specific emission. Emission from the two types of acceptors is detected separately using double detection channels, each with its own spectral filter. The resulting signal sequence consists of green signals, red signals, and no signals. In applications of PSM that involve only one type of acceptor fluorophore, the exact timing of signal detection is important to obtain the identification of the mRNA. Specific algorithms are used in that case to estimate the numbers of unlabeled tRNAs or amino acids that were processed between two consecutive labeled events (see WO2004/050825).

Figures 2, 3:
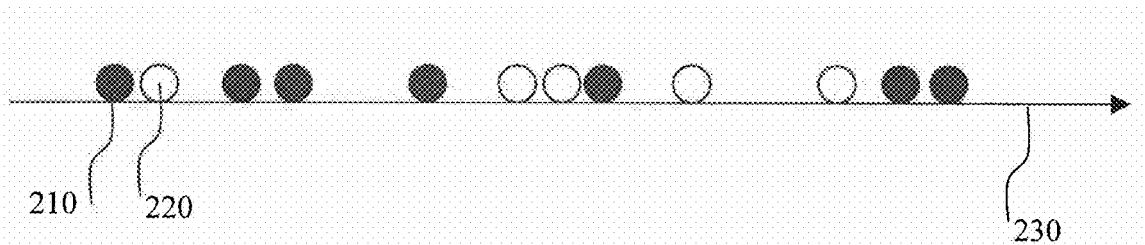
FIG. 2 describes a cartoon of FRET signal outputs from a doubly labeled synthesis system.
FIG. 3 describes the processing of an amino acid sequence into a PSM sequence for the case of double labeling.

In a preferred embodiment mRNA identification is based on the interspersion profile of red and green signals. In FIG. 2 an example is shown, where a dark disc 210 corresponds to a green signal (lysine) and an bright disc 220 to a red signal (arginine). The events are shown as they appear on temporal axis 230. This signal is translated into the code grgggrrgrrgg indicating the appearance order of green and red events. This code is used to search in an mRNA database precompiled for such searches. In FIG. 3, amino acid sequences 301 (SEQ ID NO:1) and 302 (SEQ ID NO:2) of two distinct mRNA templates are shown, with lysine (K) and arginine (R) underlined. The corresponding subsequences of lysines and arginines are shown in 303 (SEQ ID NO:3) and 304 (SEQ ID NO:4). It is clear that the code grgggrrgrrgg is compatible with sequence 303 (SEQ ID NO: 3) and not with sequence 304 (SEQ ID NO:4), and therefore matches mRNA encoding 301 (SEQ ID NO:1) but not 302 (SEQ ID NO:2). This approach serves as a basis for construction of an algorithm for mRNA identification.

Example 2 tRNA Labeling and Usage

In this preferred embodiment the acceptor fluorphore is attached to one or more species of tRNA. Methods of labeling tRNA are discussed in detail in WO2004/050825. The labeled tRNAs are known to be processed normally both by ribosome and by the cognate synthetases.

Ribosome labeling is performed using one of several preferred methods. These include labeling with naturally fluorescent proteins, with organic dyes, and with semiconductor quantum dots. Labeling strategies included labeling ribosomal proteins such as ribosomal proteins L1, S1, S21 and others; In addition, 3' and 5' ends of 5S, 16S and 23S rRNA have been labeled (Robbins and Hardesty, Biochemistry. 1983, 22; 22(24):5675-5679).

For in-vitro labeling, there are several strategies. Organic dyes can be used to label ribosomal proteins using standard protein labeling techniques. Suppliers of these dyes publish detailed protocols describing their use. General procedures label proteins through their amino groups (lysine). Other procedures target cysteines which are sometimes available for precisely located labeling. In this way, ribosomal proteins S1 and S8 were labeled by coumarin (Bakin et al., J Mol Biol., 1991 221:441-453), and ribosomal proteins were tagged with fluorescin attached to a cysteine residue (Odom et al., Biochemistry, 1990, 29:10734-10744).

A novel labeling strategy uses quantum dots, which are commercially available pre-conjugated with biotin or streptavidin. In such cases, proteins can be labeled with biotin, so the streptavidin conjugated Qdots (commercially available as Qdot™525/Qdot™ 565/Qdot™ 605/Qdot™ 655 streptavidin conjugated quantum dots, from Quantum Dot Corporation, Hayward, Calif., USA; the numbers relate to maximal emission wavelength, m) bind specifically to them. One useful method of generating a biotin-labeled protein involves creating a fusion protein between the protein of choice and biotin carboxyl carrier protein (BCCP). In the fusion protein, the original protein sequence is fused optionally to the last 87 (or 110) codons of the *E. coli* BCCP. When the fusion protein is translated, it has the biotin tag attached to it and binds specifically to streptavidin (cf. Surrey et al., Proc. Natl. Acad. Sci. USA, 95: 4293-4298, 1998).

Another method that is useful for labeling of ribosomal proteins is the well known strategy of fusing the protein of choice with a naturally fluorescent protein, such as green fluorescent protein, yellow/cyan/blue fluorescent proteins or any other naturally fluorescent protein. An example where L1 was labeled by fusing it with a naturally fluorescent protein is described in (Mascarenhas et al., EMBO Rep. 2001, 2:685-689). Numerous additional strategies for ribosome labeling were tested and others are clearly suitable for use with the present invention.

For the cell-free translation system, it is also possible to use cross systems. For example, an *E. Coli* translation system can be used for producing mammalian proteins. Alternatively, a mammalian translation system can be used. Sometimes it is beneficial to switch some system elements. For example, using some *E. Coli* tRNAs in a mammalian system can allow specific labeling of tRNAs that have appropriately modified bases. Several *E. Coli* tRNAs have the uridine in position 8 modified to thiouridine. This makes such tRNA types suitable for attaching a fluorescent label. A complete database of tRNA sequences and a database of known RNA modifications, both of which are known in the art, are hereby incorporated by reference as if fully set forth herein.

Example 3

Amino Acid Labeling

In contrast with in-vivo applications of PSM, for RNA identification amino-acid labeling could be the method of choice since the functionality of the protein is not crucial, and since amino acids can be labeled relatively easily.

There are several ways of fluorescent labeling for amino acids in a cell free translation system. One way is to introduce labeled amino acids into the system. In this case one has to verify that the cognate synthetases function normally for charging the tRNAs with the labeled amino acid. For this step, it may be required to optimize the structure of the synthetases. Methods for high-throughput adaptation of synthetases for unnatural or labeled amino acids are discussed for example in Santoro et al, Nat. Biotechnol., 20:1044-1048 2002. In such cases it is important that no unlabeled amino acid of this type exist in the system, to avoid confounding the PSM signal sequence. To achieve this, a synthetic construction of the cell free translation system is preferably prepared as described in (Shimizu et al., Nat. Biotechnol. 2001, 19:751-755), since the components of the translation system are introduced in a controlled manner.

A second way of introducing labeled amino acids is by fluorescent labeling of acylated tRNA. In other words, what is being labeled is the charged tRNA with its amino acid. Fluorescent labeled acylated tRNA can be purchased, for example the FluoroTect™ GreenLys in vitro Translation Labeling System available from Promega Corporation (Madison, Wis.). It is important in this system also that no unlabeled amino acids exist to avoid confounding the PSM signal sequence. One way to ensure this is by removing the cognate synthetases of labeled amino acids. This will ensure that recharging of tRNA does not occur, and only the labeled tRNA that was introduced will be used.

Example 4

Additional PSM Strategies

In one preferred embodiment, a quenching strategy is used instead of FRET, as noted previously. Accordingly, instead of a fluorescent donor and acceptor, there is a fluorescent donor and an acceptor quencher that captures the donor energy without emission. Donor fluorescence is detected as long as the quencher is not sufficiently near to the donor. Use of this strategy in PSM, generates a signal of donor fluorescence intermitted by periods of quenching.

In another preferred embodiment, a combination of methods is used. For example, some tRNAs and some amino acids may be labeled as acceptors, either with distinct or with indistinguishable optical characteristics. Preferably, the amino acids are labeled with fluorescent labels that are distinct from tRNA labels. The signal analysis system accepts both signals and uses both in order to identify more confidently the mRNA being translated. It is obvious to anyone skilled in the art of single molecule detection and analysis that this is just one example of a wide variety of methods that can be derived from this particular example.

In view of the large number of possible applications and embodiments of the present disclosure it should be recognized that the illustrated embodiments are only particular examples and should not be taken as a limitation on the scope of the disclosure. Some of the possible additional applications which are clearly enabled by the present invention are clinical applications, diagnostic applications, production of food, cosmetics, and other bioproducts, military applications concerning biological warfare, and many more.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

The invention claimed is:

1. A method for mRNA identification, the method comprising:
 (a) providing a protein synthesis monitoring (PSM) system, wherein the PSM system comprises:
  (i) at least two distinct fluorophore donor-acceptor pairs each consisting of a donor fluorophore and a matching acceptor fluorophore, the acceptor fluorophore of each pair being bound to a ribosome or a fragment thereof, the ribosome or the fragment thereof being attached to a solid substrate, and the donor fluorophore of each pair being bound to at least two aminoacyl-tRNAs or at least two amino acids, wherein each donor-acceptor pair is capable of emitting electromagnetic radiation in response to translation activity;

(ii) elongation factors and energy sources; and
(iii) a detection apparatus for measuring radiation emitted from the at least two distinct fluorophore donor-acceptor pairs of the PSM system;
(b) introducing at least one mRNA molecule into the PSM system, wherein the sequence of the at least one mRNA molecule is present in a precompiled mRNA database;
(c) detecting electromagnetic radiation signals obtained in response to translation activity; and
(d) identifying one or more mRNA molecules in the precompiled mRNA database that are plausible generators of the electromagnetic radiation signals; comprising:
   obtaining an interspersion profile of at least one signal sequence emitted from said at least two fluorophore donor-acceptor pairs;
   performing PSM database interrogation in said precompiled mRNA database, comprising:
   determining a probability of an mRNA molecule in the precompiled mRNA database to generate said at least one signal sequence;
   selecting one or more mRNA molecules in the precompiled mRNA database as having a highest scoring function value; and
   assigning said one or more mRNA molecules in the precompiled mRNA database as plausible generators of said at least one signal sequence, thereby assigning one or more mRNA molecules in the precompiled database to said at least one mRNA molecule.

2. The method of claim 1, comprising introducing a plurality of mRNA molecules into the PSM system.

3. The method according to claim 1, wherein the solid substrate is selected from the group consisting of: glass, glass slide adapted for a microscope and a solid substrate having a mica surface.

4. The method according to claim 1, wherein the at least one signal sequence is composed of one or more values selected from the group consisting of: time, spatial coordinates, signal type and signal intensity.

5. The method according to claim 1, wherein the signals are obtained by energy transfer between the donor fluorophore and the matching acceptor fluorophore.

6. The method according to claim 5, wherein the signals are FRET signals.

7. The method according to claim 1, wherein each fluorophore donor-acceptor pair is a label selected from the group consisting of: an organic dye, and a quantum dot.

8. The method according to claim 1, wherein the ribosomal fragment is selected from the group consisting of: ribosomal RNA, a ribosomal protein, ribosomal protein L1, ribosomal protein L11, ribosomal protein S1 and fragments thereof.

9. The method according to claim 8, wherein the ribosomal fragment is located near a ribosomal site selected from the group consisting of: ribosomal A site, ribosomal P site, ribosomal E site, peptide exit channel site, L1 arm, and L7/L12 arm.

10. The method according to claim 1, wherein the PSM system comprises:
   a plurality of distinct fluorophore donor-acceptor pairs detectable through detection of electromagnetic radiation, wherein each pair comprises a FRET pair of interacting labeling moieties, a first moiety of each pair being bound to a ribosome fragment and a second moiety of each pair being bound to an aminoacyl-tRNA, wherein each pair is capable of emitting electromagnetic radiation in response to translation activity.

11. The method of claim 10, wherein at least one pair of said plurality of pairs is one of two distinct colors.

12. The method of claim 1, wherein the acceptor fluorophore is the same fluorophore in each of said at least two distinct fluorophore donor-acceptor pairs.

13. The method of claim 1, wherein the PSM system further comprises initiation factors.

14. The method of claim 13, wherein the PSM system further comprises at least one translation component selected from the group consisting of: aminoacyl-tRNA synthetases, termination factors and energy regenerating molecules.

15. The method of claim 1, wherein the detection apparatus comprises an image acquisition device configured to acquire data that permits optical resolution of the fluorophore donor-acceptor pairs.

\* \* \* \* \*

SEQUENCE LISTING

```
<160> NUMBER OF SEQ ID NOS: 4

<210> SEQ ID NO 1
<211> LENGTH: 89
<212> TYPE: PRT
<213> ORGANISM: Artificial Sequence
<220> FEATURE:
<223> OTHER INFORMATION: Synthetic peptide

<400> SEQUENCE: 1
```

-continued

```
Val Gly Ser Asp Lys Cys Thr Thr Ile His Tyr Asn Tyr Met Cys Asn
1               5                   10                  15

Arg Ser Ser Cys Met Gly Gln Leu Lys Lys Trp Val Asp Ser Thr Pro
            20                  25                  30

Lys Pro Pro Gly Thr Arg Val Arg Lys Ala Met Ala Ile Tyr Gln Ser
        35                  40                  45

Arg Arg Gln His Met Thr Glu Val Val Ser Val Thr Lys Cys Thr Tyr
    50                  55                  60

Ser Pro Ala Leu Asn Val Gln Leu Val Lys Glu Ser Gly Gly Gly Arg
65                  70                  75                  80

Leu Val Gln Pro Gly Gly Ser Leu Arg
                85
```

<210> SEQ ID NO 2
<211> LENGTH: 80
<212> TYPE: PRT
<213> ORGANISM: Artificial Sequence
<220> FEATURE:
<223> OTHER INFORMATION: Synthetic peptide

<400> SEQUENCE: 2

```
Ser Cys Ala Ala Ser Gly Tyr Thr Phe Thr Asn Tyr Gly Met Asn Trp
1               5                   10                  15

Val Arg Gln Gln Asp Gln Pro Met Arg Glu Glu Glu Val Glu Thr
            20                  25                  30

Phe Ala Phe Gln Ala Glu Ile Ala Gln Leu Met Ser Leu Ile Ile Asn
        35                  40                  45

Thr Phe Tyr Ser Asn Lys Glu Ile Phe Leu Arg Glu Asn Ser Ser Asp
    50                  55                  60

Ala Leu Asp Lys Thr Ile Ala Lys Ser Gly Thr Lys Ala Phe Met Glu
65                  70                  75                  80
```

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

```
Lys Arg Lys Lys Lys Arg Arg Lys Arg Arg Lys Lys
1               5                   10
```

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

```
Arg Lys Arg Arg Lys Lys Lys
1               5
```